United States Patent
Aguado et al.

(10) Patent No.: US 9,937,317 B2
(45) Date of Patent: Apr. 10, 2018

(54) MODIFIED MEDICAL SYRINGE WITH A FLOW REGULATOR FOR THE ADMINISTRATION OF LOCAL ANAESTHETIC

(71) Applicant: IPSUMPRO, S.L., Valencia (ES)

(72) Inventors: Roberto Garcia Aguado, Valencia (ES); Jorge Ubeda Pascual, Valencia (ES)

(73) Assignee: IPSUMPRO, S.L., Valencia (ES)

( * ) Notice: Subject to any disclaimer, the term of this patent is extended or adjusted under 35 U.S.C. 154(b) by 30 days.

(21) Appl. No.: 15/182,249

(22) Filed: Jun. 14, 2016

(65) Prior Publication Data

US 2016/0287836 A1 Oct. 6, 2016

Related U.S. Application Data

(63) Continuation-in-part of application No. 14/375,471, filed as application No. PCT/ES2012/070048 on Jan. 30, 2012, now Pat. No. 9,364,607.

(51) Int. Cl.
*A61M 19/00* (2006.01)
*A61M 5/31* (2006.01)
(Continued)

(52) U.S. Cl.
CPC .......... *A61M 19/00* (2013.01); *A61M 5/3129* (2013.01); *A61M 5/31511* (2013.01); *A61N 1/0502* (2013.01); *A61N 1/0551* (2013.01)

(58) Field of Classification Search
CPC ........ A61M 5/31511; A61M 25/10182; A61M 5/31501; A61M 5/204; A61M 2005/5026; A61M 5/1782
See application file for complete search history.

(56) References Cited

U.S. PATENT DOCUMENTS

| 2,841,145 A | * | 7/1958 | Epps | A61M 5/284 604/89 |
| 3,052,239 A | * | 9/1962 | Silver | A61M 5/284 604/89 |

(Continued)

FOREIGN PATENT DOCUMENTS

| AT | 406121 B | 2/2000 |
| DE | 19807487 A | 8/1999 |

(Continued)

*Primary Examiner* — Scott Medway
(74) *Attorney, Agent, or Firm* — Garcia-Zamor IP Law; Ruy M. Garcia-Zamor

(57) ABSTRACT

Modified medical syringe with a flow regulator for the administration of anaesthesia, which allows for anaesthesiologists to handle the needle, control continuous aspiration and administer the anaesthetic with a single hand, thereby preventing intravascular injections. It comprises a flexible tube, designed to be introduced inside the barrel, which supplies the anaesthetic; a cylindrical body located on the rod, equipped with a protuberance along a semicircle located on the proximal side of the body and a through-hole wherein one end of the flexible tube may be introduced; a cylindrical cap located inside the syringe barrel, equipped with a longitudinal groove along its cylindrical side, which is designed to house the aforementioned flexible tube; a preloaded spring around the rod located between the cap and the support disk; and a pressurization device connected to the flexible tube.

17 Claims, 10 Drawing Sheets

(51) Int. Cl.
*A61M 5/315* (2006.01)
*A61N 1/05* (2006.01)

(56) References Cited

U.S. PATENT DOCUMENTS

| | | | | |
|---|---|---|---|---|
| 3,680,558 A | * | 8/1972 | Kapelowitz | A61B 5/15003 604/89 |
| 3,698,453 A | * | 10/1972 | Morane | B65D 83/682 141/20 |
| 3,729,031 A | * | 4/1973 | Baldwin | A61M 5/1782 141/2 |
| 3,767,085 A | * | 10/1973 | Cannon | A61C 9/0026 222/137 |
| 3,785,379 A | * | 1/1974 | Cohen | A61M 5/31596 604/88 |
| 3,957,082 A | | 5/1976 | Fuson | |
| 4,014,330 A | * | 3/1977 | Genese | A61M 5/2429 604/88 |
| 4,188,949 A | * | 2/1980 | Antoshkiw | A61M 3/005 604/191 |
| 4,269,174 A | | 5/1981 | Adair | |
| 4,476,866 A | * | 10/1984 | Chin | A61M 25/10182 604/271 |
| 5,067,948 A | * | 11/1991 | Haber | A61M 5/2448 604/192 |
| 5,147,329 A | * | 9/1992 | Brannon | A61B 5/15003 600/577 |
| 5,247,966 A | | 9/1993 | Stevens | |
| 5,599,312 A | * | 2/1997 | Higashikawa | A61M 5/19 604/191 |
| 5,630,800 A | * | 5/1997 | Blank | A61M 5/31596 604/228 |
| RE36,273 E | * | 8/1999 | Brannon | A61B 5/15003 600/578 |
| 6,379,328 B1 | * | 4/2002 | MacClay | A61M 5/31525 604/191 |
| 6,595,956 B1 | * | 7/2003 | Gross | A61M 5/14248 128/DIG. 12 |
| 9,751,056 B2 | * | 9/2017 | McArthur | B01F 13/0023 |
| 2002/0022804 A1 | * | 2/2002 | Connolly | A61J 1/2089 604/201 |
| 2005/0027262 A1 | | 2/2005 | Appling | |
| 2006/0079834 A1 | * | 4/2006 | Tennican | A61J 1/2096 604/88 |
| 2006/0258977 A1 | * | 11/2006 | Lee | A61M 5/31596 604/82 |
| 2006/0278588 A1 | * | 12/2006 | Woodell-May | B01L 3/502 210/787 |
| 2006/0280690 A1 | * | 12/2006 | Wright | A61B 17/00008 424/45 |
| 2007/0003488 A1 | * | 1/2007 | Wright | A61B 17/00008 424/47 |
| 2007/0267092 A1 | * | 11/2007 | Rink | B65B 3/003 141/65 |
| 2008/0255523 A1 | * | 10/2008 | Grinberg | A61M 5/008 604/192 |
| 2009/0163860 A1 | | 6/2009 | Patrick | |
| 2010/0292672 A1 | * | 11/2010 | Lee | A61M 5/31596 604/518 |
| 2011/0319862 A1 | * | 12/2011 | Friedman | A61M 5/16804 604/500 |
| 2012/0029471 A1 | * | 2/2012 | Lee | A61M 5/19 604/518 |
| 2015/0190125 A1 | * | 7/2015 | Hwang | A61B 10/0283 600/578 |
| 2017/0203047 A1 | * | 7/2017 | Orofino | A61M 5/204 |

FOREIGN PATENT DOCUMENTS

| | | |
|---|---|---|
| EP | 0732120 A1 | 9/1996 |
| EP | 1002500 A | 5/2000 |
| EP | 1205156 A2 | 5/2002 |
| GB | 2425484 | 11/2006 |
| WO | WO2002055145 | 7/2002 |
| WO | WO2004032995 | 4/2004 |

\* cited by examiner

MODIFIED MEDICAL SYRINGE WITH A FLOW REGULATOR FOR THE ADMINISTRATION OF LOCAL ANAESTHETIC

CROSS-REFERENCE TO RELATED APPLICATIONS

This application claims priority to and is a continuation in part of U.S. patent application Ser. No. 14/375,471, filed Feb. 25, 2015, and also claims priority to PCT application PCT/ES2012/070048, filed Jan. 30, 2012; each of the above referenced applications is hereby incorporated by reference herein as if fully set forth in its entirety.

DESCRIPTION

Object of the Invention

The object of the present invention is a novel device that involves the modification of a medical syringe in order to regulate administration of local anaesthetic. The invention allows for anaesthesiologists to control the administration of a local anaesthetic with the same hand that handles the needle when performing nerve blocks.

BACKGROUND OF THE INVENTION

Nerve blocks are an increasingly used option for providing adequate surgical anaesthesia, post-operative analgesia or treating various chronic pathologies; it is performed by depositing a local anaesthetic, at sufficient volume and concentration, at the adequate site or sites by means of a needle; i.e. as close as possible to the nerves without puncturing the blood vessels that accompany them. To this end, it is very important to always perform aspiration prior to the injection.

As may be seen from the preceding paragraph, performing a correct nerve block is dependent upon the location of the areas of the body where the anaesthetic is to be applied, on the basis of anatomical references or the use of neurostimulation devices or ultrasound and ultrasonography techniques.

The fact that anaesthesiologists use ultrasound scanning or neurostimulation in order to locate the nerves to be blocked entails that one of their hands handles the device whilst the other handles the needle; for this reason, controlling both the aspiration and the administration of the anaesthetic to be injected must be left to another person or requires complex contraptions that may be handled with other parts of the body, for example, the feet, by pressing down a pedal.

The present invention proposes a device that allows for anaesthesiologists to handle the needle and continuously control both aspiration and administration of the anaesthetic when desired, with a single hand, thereby preventing potential undesirable intravascular injections.

DESCRIPTION OF THE INVENTION

The modified medical syringe with a flow regulator for the administration of anaesthesia of the present invention comprises a flexible tube designed to be introduced inside the syringe barrel, which supplies a fluid; a cylindrical body located at the distal end of the piston rod, the diameter whereof is smaller than the inner diameter of the syringe barrel and larger than the diameter of the piston rod, said body being equipped with: a watertight gasket between the body and the syringe barrel; a protuberance along a semicircle on the proximal side of the body, the centre whereof is located on the axis of revolution of said body; and a through-hole between its distal side and its proximal side, designed to introduce one of the ends of the flexible tube therein, the end of the aforementioned through-hole located on the proximal side of the body being placed between the protuberance and the piston rod; a cylindrical cap located inside the syringe barrel, equipped with a longitudinal groove along its cylindrical side, which is designed to house the aforementioned flexible tube and comprises a central hole for the piston rod; a preloaded spring placed around the piston rod, between the cap and the support disk of the aforementioned piston, such that, when no compressive force is exerted on said spring, the proximal side of the body is in contact with the distal side of the cap and a fluid pressurisation device connected to the free end of the flexible tube.

BRIEF DESCRIPTION OF THE FIGURES

Following is a brief description of a series of drawings that help to better understand the invention and which are expressly related to an embodiment of said invention, presented as a non-limiting example thereof.

PREFERRED EMBODIMENTS

Figure 1:
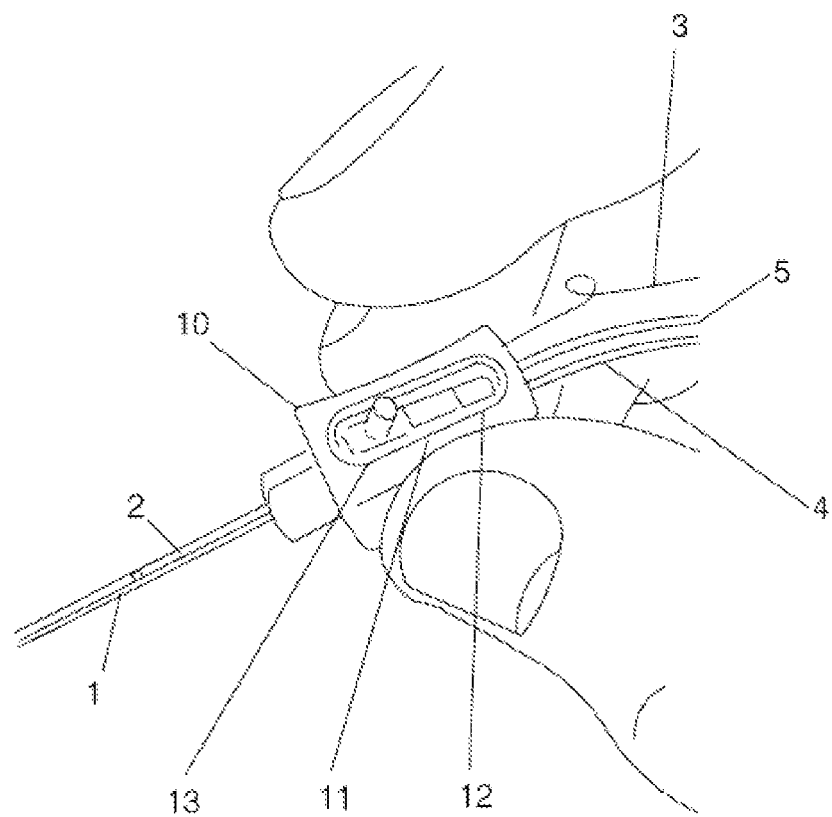
FIG. 1 shows an image of the controlled-flow needle with the three position possibilities: R1: "neutral", R2: Suction; R3: "administration".
Figure 2:
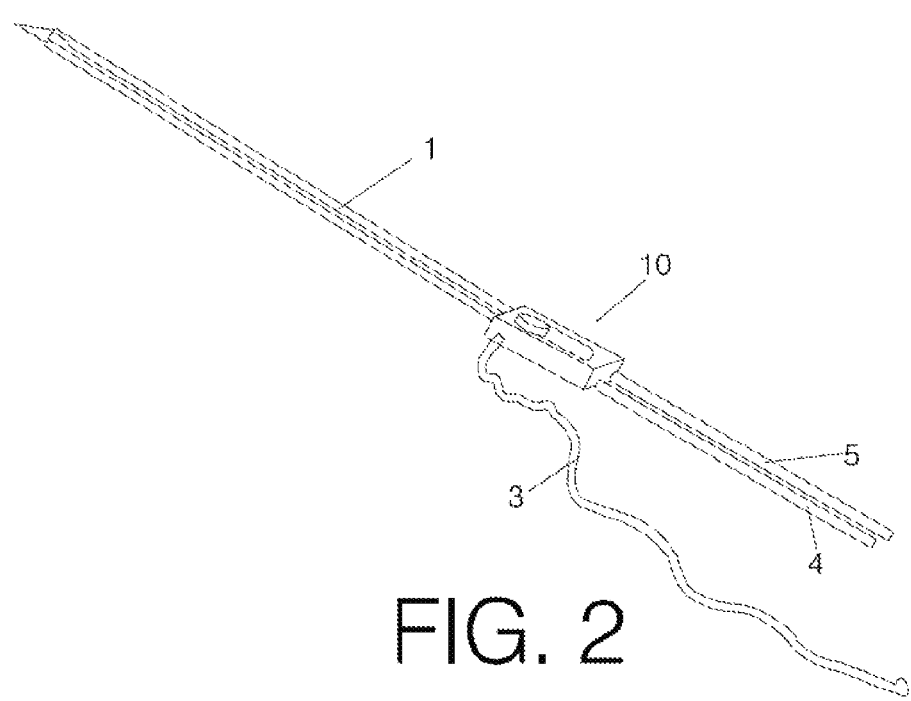
FIG. 2 shows an external diagram of the controller with the slidable pusher.
Figure 3A:
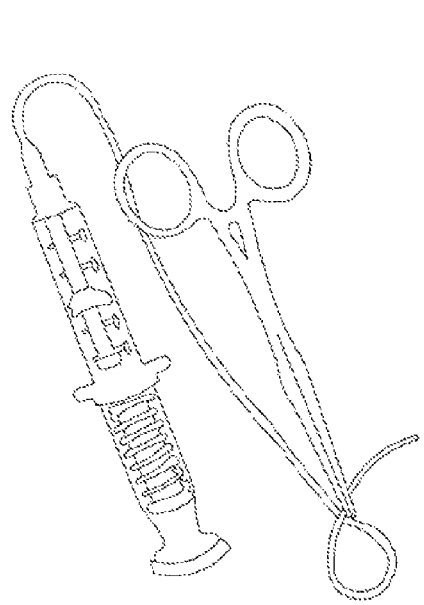
FIG. 3A shows a syringe with mechanical-type (spring) positive suction and pressure system. The line connected to the syringe is shown, displaying the effect of the suction.
Figure 3B:
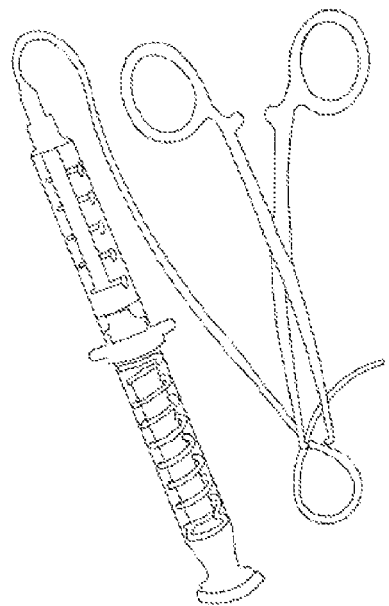
FIG. 3B shows a syringe with mechanical-type (spring) positive suction and pressure system. The line connected to the syringe is shown, displaying the effect of the loss of suction.
Figure 3C:
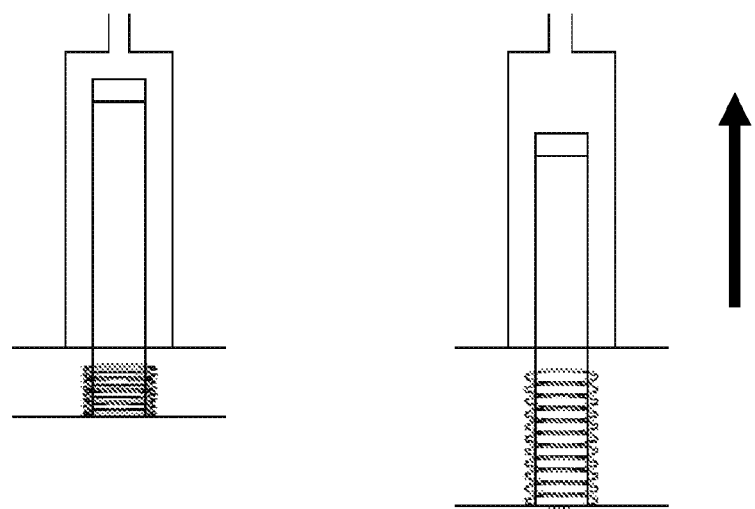
FIG. 3C shows syringes with mechanical-type (spring) positive suction and pressure system. This figure shows the syringe with the reverse spring for connecting to the administration line (positive pressure).
Figures 4A, 4B:
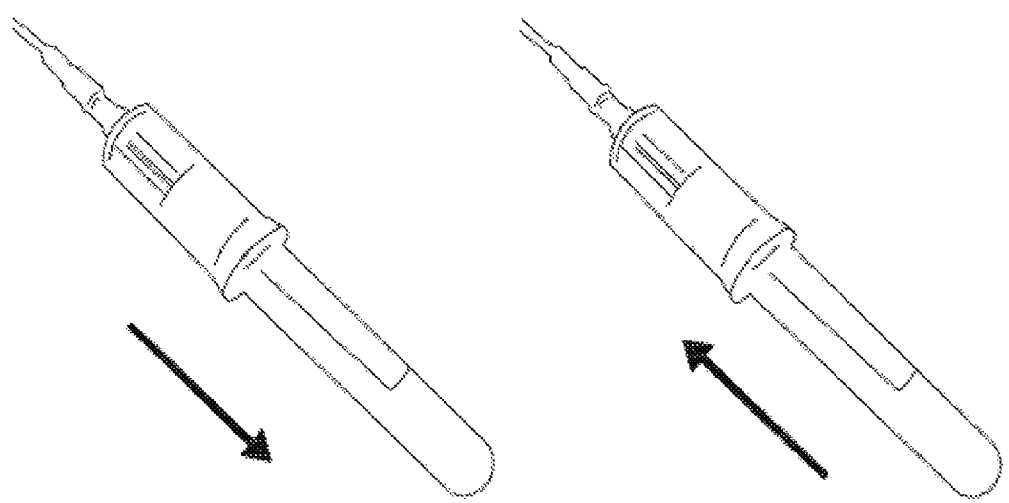
FIG. 4A shows the syringes with "vacutainer"® type positive suction and pressure system.
FIG. 4B shows the syringes with "vacutainer"® type positive suction and pressure system.

One embodiment of the present invention proposes a controlled-flow needle that includes means for controlling fluid flow in the needle which allow, manually and at will by the dominant hand of the anaesthesiologist performing the nerve block, both the timing and volume required during the performance of the technique, obviating the need for a collaborator and thereby increasing the effectiveness, speed and safety of the procedure.

As can be observed in the attached figures, the controlled-flow needle object of the present invention comprises, at least:

A needle or cannula (1) with standard coating for performing nerve blocks, with or without neurostimulation. In a particular embodiment a 21 G caliber needle is preferably used.

An outer sheath (2) over the needle (1) with a flange for sliding it upon administering the local anaesthetic and which also allows the passage of a catheter if necessary.

A cable for electrostimulation (3).

An independent line for administering local anaesthetic (4).

An independent line for suction (5).

A flow controller element (10) which moves from the suction position (11) to the administration position (12). It is indistinct whether the sliding is in the direction of the needle (1) axis or transversely thereto.

A pressurised syringe with or without local anaesthetic (between 5 ml and 20 ml depending on the application).

A mechanical suction syringe, i.e. having a spring in the plunger, or a "vacutainer"® type vacuum syringe.

The flow control element (10) is manual, mechanical and sliding. This controller has three positions: neutral (13), suction (11) and administration (12). The neutral position (13) does not administer or suction, and is constituted at the starting point. The suction position (11) is the position where the independent suction line (5) remains open and is also the position to which the flow controller (10) will return, provided that the fluid administration position (12) does not remain activated.

Figure 5A:
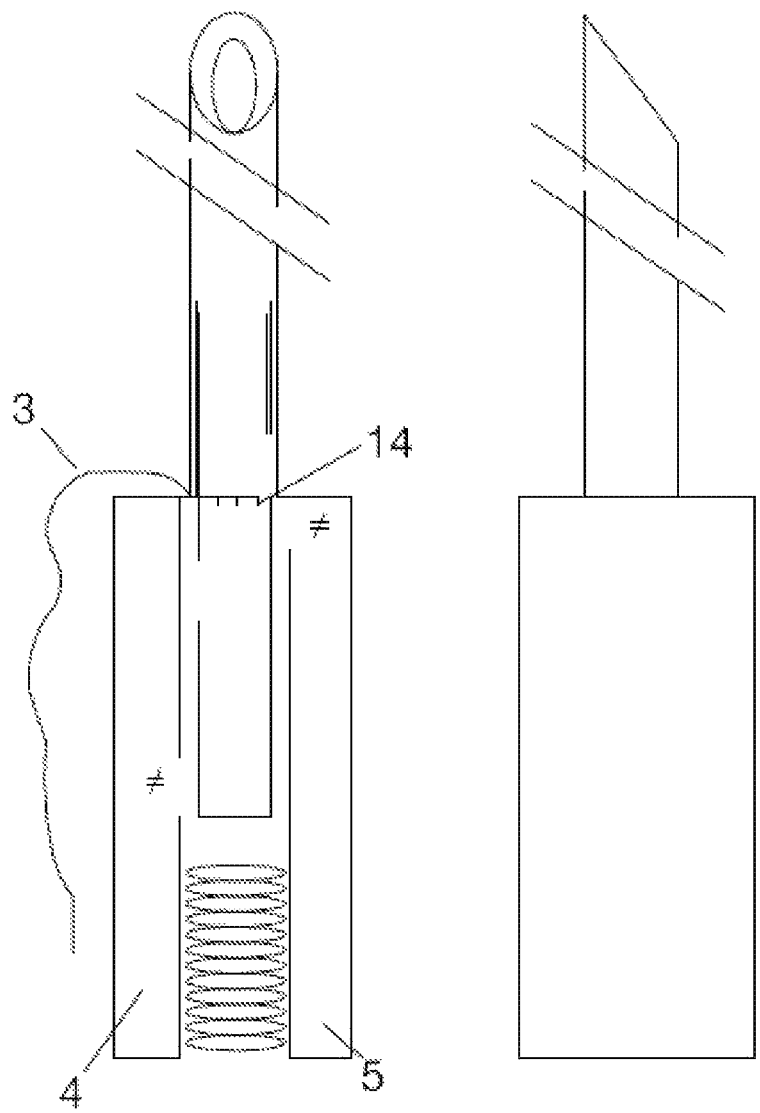
FIG. 5A shows an internal diagram of the controller (FIG. 5A) showing the controller sliding in the direction of the needle axis.
Figures 5B, 5C:
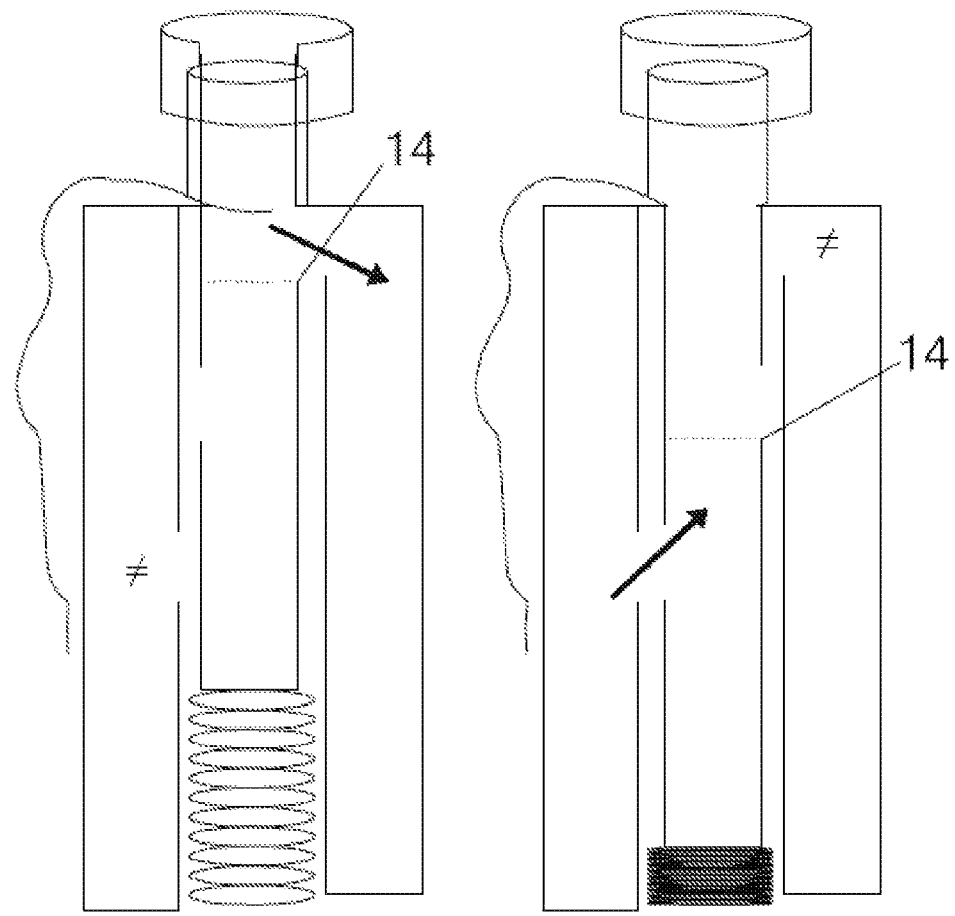
FIG. 5B shows the controller in the suction position.
FIG. 5C shows the controller in the administration position.

The flow controller (10) comprises two particular embodiments:

Sliding in the direction of the needle, where the controller can be located on one of the sides, preferably in the upper position, to be slid using the index finger. In FIG. 5a, it begins in a neutral position (13) where, after the puncture, the controller is slid towards a first suction position (11), as can be observed in FIG. 5b, in correspondence with the independent suction line (5), position to which the controller will always return provided that the anaesthesiologist does not maintain the second administration position (12) activated, in correspondence with the independent administration line (4), FIG. 5c.

Figure 6A:
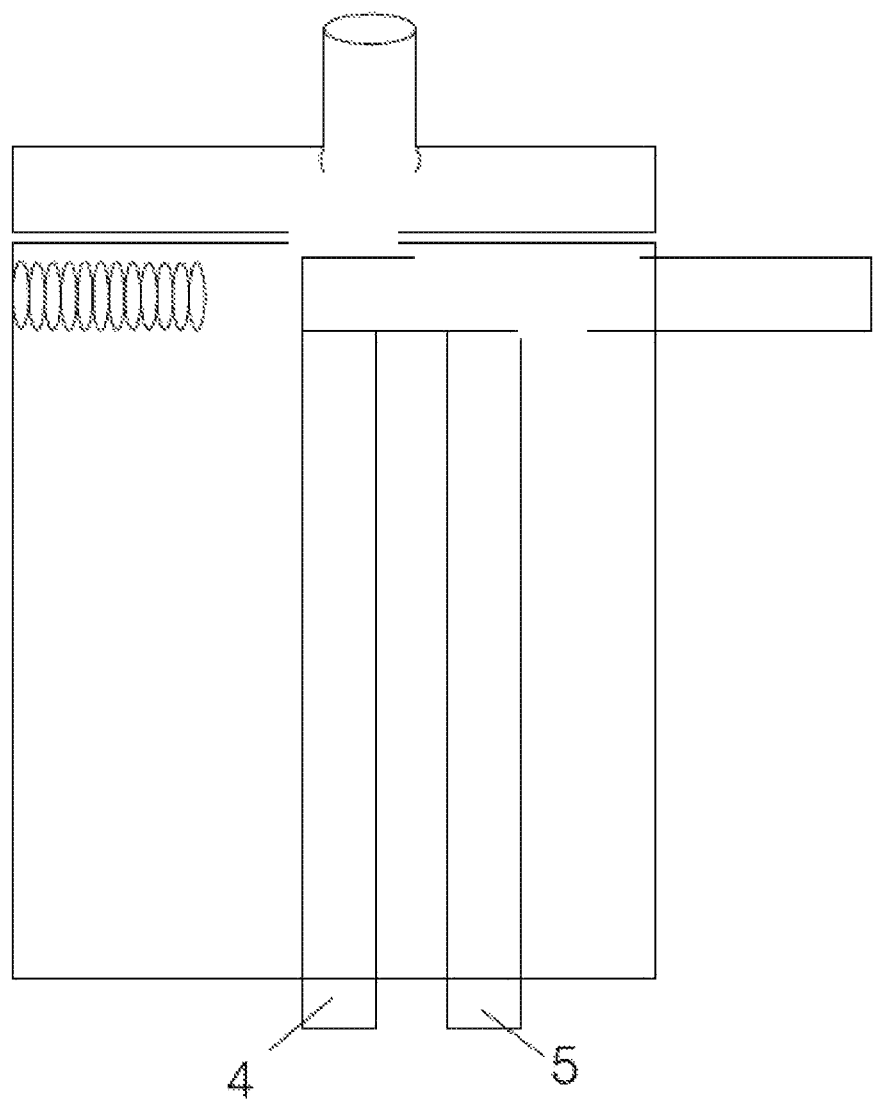
FIG. 6A shows an internal diagram of the controller showing the controller sliding transversely to the needle axis.
Figure 6B:
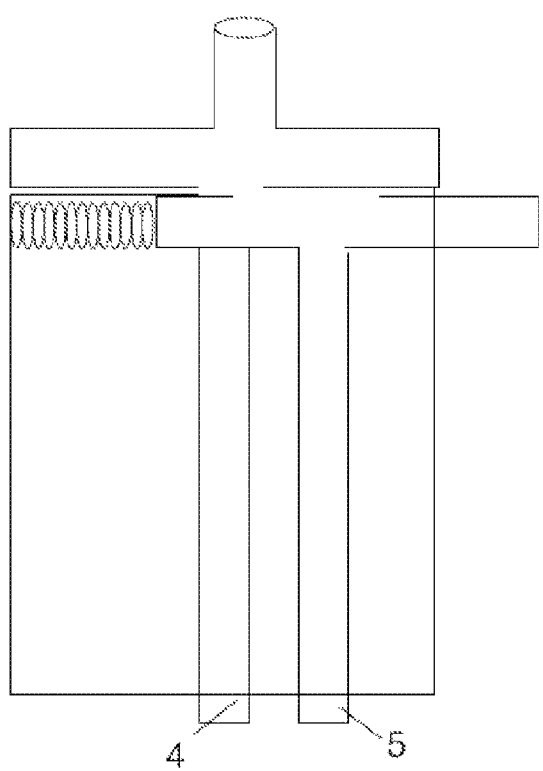
FIG. 6B shows an internal diagram of the controller showing the controller in the suction position.
Figure 6C:
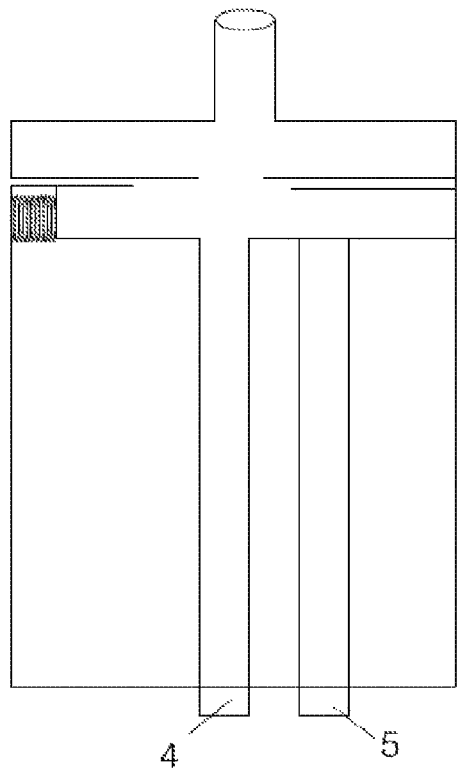
FIG. 6C shows an internal diagram of the controller showing the controller in the administration position.

Transverse sliding in the direction of the needle, where the controller can be located on one of the sides to be pressed. As in the previous embodiment, the controller begins in a neutral position (13), FIG. 6a, and after the puncture, the first working position or suction position (11) is slid or pressed in correspondence with the independent suction line (5), FIG. 6b, position to which the controller will always return provided that the anaesthesiologist does not maintain a second administration position (12) activated, in correspondence with the independent administration line (4), FIG. 6c.

In both options, the dotted line represents a resistance (14) that must be overcome from the neutral position (13) before moving to the suction position (11). This resistance (14) is materialised in a ring or protuberance that hampers sliding (option (a)) or pressure (option (b)). Therefore, when the pressure ceases, it will never move to the neutral position unless purposefully actuated, for example at the start of the procedure or priming. The use of the needle object of the present invention begins with a first stage of preparation or priming, performed in the same manner as in the current state of the art. The purpose is to avoid the introduction of air bubbles which, in the case of ultrasound, also hampers the view of the images due to the opacity of the air for the ultrasound waves. Therefore, in a first phase, with the controller element (10) in the neutral position (13), the independent administration line (4) is connected to a pressurised syringe with the system defined and the independent suction line (5) is left open. Subsequently, the controller is moved to the administration position (12) until the local anaesthetic flows out of the needle tip (1). At that moment the administration is suspended and controller returns to the neutral position (13). At that moment, connection can be made to the independent administration line (5) and the device is ready for use.

Once the needle object of the invention has been primed, the anaesthesiologist can, in a self-sufficient manner and without need for an external collaborator, perform the technique correctly and safely. Once the needle punctures the skin, the controller is moved to the first working position, i.e. to the suction position (11), in such a manner that what happens to the needle tip will be under permanent suction conditions. This guarantees that the needle tip (1) is not intravascular, preventing systemic toxicities or damage to any vascular structure during the progress of the needle (1). This implies an improvement in whatever technique is used to detect the nerve in question during this phase.

Once the nerve to be blocked has been located, whether via neurostimulation and/or ultrasound, the anaesthesiologist, using the hand that performs the puncture, will proceed to administer or dissect the tissues with the local anaesthetic, surrounding and thereby adapting the distribution of the anaesthetic around the nerve to be blocked.

The combination of the progress of the needle and the displacement of the tissues by the injection of local anaesthetic is significantly improved by the invention, as it is the anaesthesiologist who controls the time and volume of the anaesthetic he/she administers in a dynamic and synchronised manner, facilitating the positioning of the needle in the exact location and avoiding obstacles by means of careful hydrodissection.

Similarly, it is sufficient to cease the pressure/displacement during administration and the controller will return to the suction position (11) as many times as required, as the vacuum syringe, unless it suctions due to inadvertent vascular puncture, should not lose significant volume as no air is suctioned in the tissues.

The level of sensitivity is also better than if performed using a pedal-type system or with an assistant, as the controller element (10) is held in the anaesthesiologist's dominant hand and index finger thereof, on the same progressing needle (1).

Lastly, the response time, which is also important, is immediate in the invention with respect to other remotely controlled drug pumps, as the length of the line mitigates the response to changes in pressure and the volume administered is modified.

Although the device described is essentially manual, it is evident to a person skilled in the art that an obvious evolution of the invention would be the remote control thereof. This would be carried out on the basis of the concept advocated in the present invention wherethrough it is controlled by the anaesthesiologist's hand, but using a remote control. Therefore, using a wireless system and the same three positions as the described controller, fluid suction or administration commands would be sent to a peristaltic pump.

Figure 7:
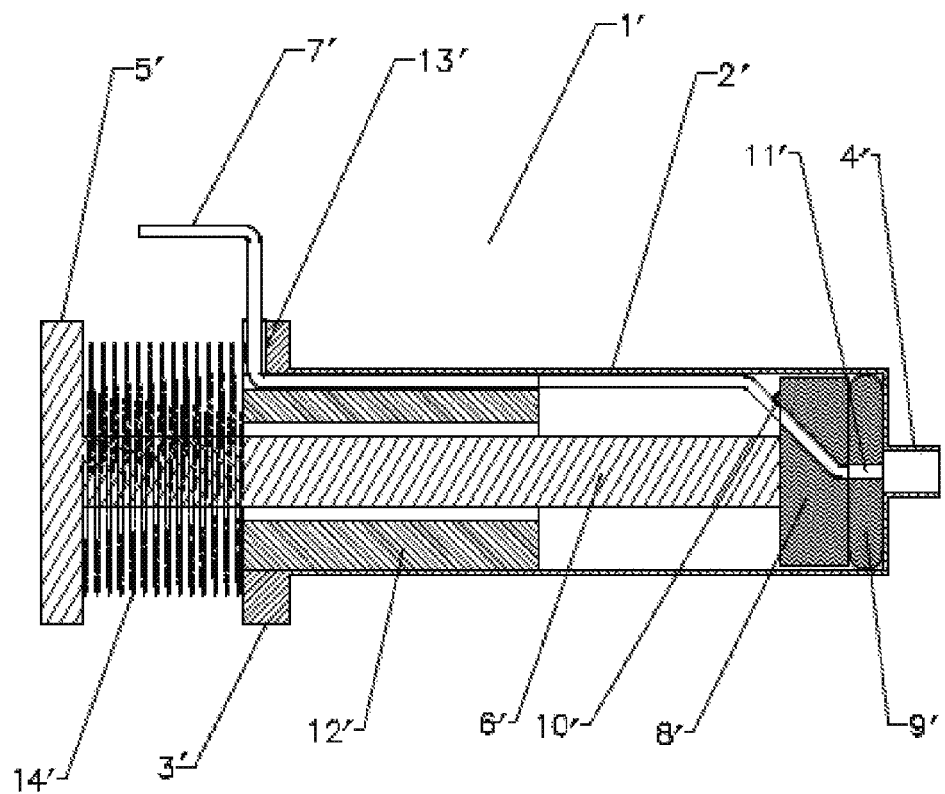
FIG. 7: Shows a view of a longitudinal section of the modified medical syringe with a flow regulator for the administration of local anaesthetic when the fluid passage is closed.
Figure 8:
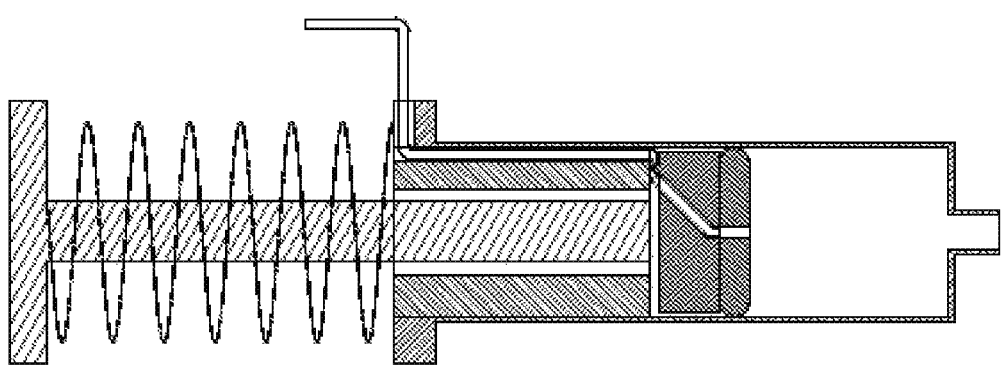
FIG. 8: Shows a view of a longitudinal section of the modified medical syringe with a flow regulator for the administration of local anaesthetic when the fluid passage is open.

FIGS. 7 and 8 show another preferred embodiment of the modified medical syringe with a flow regulator for the administration of anaesthesia of the present description.

The modified medical syringe with a flow regulator for the administration of anaesthesia (1') is of the type that comprises a transparent barrel (2') equipped with a support (3') at the proximal end and a connector (4'), preferably of the "luer-lock", or "LL", type, in order to attach a puncture needle thereto, and a piston with its corresponding support disk (5') and piston rod (6').

In this preferred embodiment, the modified medical syringe with a flow regulator for the administration of anaesthesia (1') comprises a flexible tube (7') designed to be introduced inside the syringe barrel, which supplies a fluid, i.e. one of the ends thereof is inside the barrel (2') and the other end is connected to a fluid pressurisation device, preferably another syringe, intravenous fluid recipient or elastomer; a cylindrical body (8') located at the distal end of the piston rod (6'), the diameter whereof is smaller than the inner diameter of the syringe barrel (2') and larger than the diameter of the piston rod (6'), said body (8') being equipped with: a watertight gasket (9') between the body and the syringe barrel; a protuberance (10') along a semicircle on the proximal side of the body (9'), the centre whereof is located on the axis of revolution of said body (8'); and a through-hole (11') between its distal side and its proximal side, designed to introduce one of the ends of the flexible tube (7') therein, the end of the aforementioned through-hole (11') on the proximal side of the body being placed between the protuberance and the piston rod, and the other end of the aforementioned through-hole preferably being placed on the axis of revolution of the body; a cylindrical cap (12') located inside the syringe barrel, equipped with a longitudinal groove (13') along its cylindrical side, which is designed to house the aforementioned flexible tube; preferably, the proximal side of the syringe barrel support is equipped with a radial slot designed to house the flexible tube; a preloaded spring (14') placed around the piston rod between the cap and the support disk of the aforementioned piston, such that, when no compressive force is exerted on said spring, the proximal side of the body is in contact with the distal side of the cap and a fluid pressurisation device connected to the free end of the flexible tube.

In this preferred embodiment, the proximal side of the syringe barrel support is equipped with a radial slot designed to house the flexible tube, and the cap and the syringe barrel support may form a single piece.

The process for using the present preferred embodiment of the modified medical syringe with a flow regulator for the administration of anaesthesia is as follows:

a) An adequate needle is coupled to the modified medical syringe with a flow regulator for the administration of local anaesthetic.

b) The flexible tube is connected to the other syringe, fluid recipient or elastomer which contains the anaesthetic fluid.

c) The circuit formed by the other syringe, the flexible tube and the modified medical syringe with a flow regulator for the administration of local anaesthetic is pressurised.

d) Pressure is put on the piston, which opens the circuit; thus, the fluid fills the barrel and flows through the needle, whilst purging the air from the circuit.

e) The puncture is performed.

f) Once the skin has been pierced, pressure is no longer put on the piston; this causes the spring to move the body towards the cap and the flexible tube is trapped between the protuberance and the cap, which closes the circuit and creates a negative pressure inside the barrel, thereby producing continuous aspiration.

g) The puncturing technique is continued until the adequate depth is reached; should a blood vessel be pierced during this step, since there is a negative pressure inside the barrel, the blood would flow towards the interior of the syringe, which would allow for the anaesthesiologist to detect it.

h) Pressure is put on the piston in order to inject the anaesthetic to the patient.

If the process wants to be repeated, the circuit would have to be re-pressurised.

The invention claimed is:

1. Modified medical syringe with a flow regulator for the administration of anaesthesia, comprising:

a syringe barrel having an inner diameter, a flexible tube designed to be introduced inside the syringe barrel, which supplies a fluid, the flexible tube having a proximal tube end and a distal tube end, the distal tube end being located in the syringe barrel;

a piston rod moveably located within the syringe barrel and having a piston diameter, the piston rod having a cylindrical body located at a distal end thereof, the piston rod having a distal piston rod end located in the syringe barrel and having a proximal piston rod end, a support disk located on the proximal piston rod end configured to facilitate depressing the piston rod, the cylindrical body having a diameter that is smaller than the inner diameter of the syringe barrel and larger than the piston rod diameter the cylindrical body being equipped with: a gasket configured to form a watertight seal between the cylindrical body and the syringe barrel;

a protuberance positioned on a proximal side of the cylindrical body, a radial center of the protuberance is radially offset from a radial center of the cylindrical body;

the cylindrical body defining a through-hole between a distal side thereof and the proximal side, the through-hole is configured to receive the distal tube end therein, an opening to the through-hole is located on the proximal side of the cylindrical body and is radially positioned between the protuberance and the piston rod;

a cylindrical cap located inside the syringe barrel, equipped with a longitudinal groove along a radially outer surface thereof which is designed to house the flexible tube, the cylindrical cap comprises a central hole for the piston rod and a distal cap side in facing opposition with the proximal side of the cylindrical cap;

a preloaded spring is located around the piston rod and located between the cylindrical cap and the support disk of the piston rod, such that, when no compressive force is exerted on said spring, the proximal side of the cylindrical body is in contact with the distal side of the cylindrical cap, the modified medical syringe being configured such that when the proximal side of the cylindrical body is in contact with distal side of the cylindrical cap that flow of fluid from the proximal tube end to the distal tube end is interrupted.

2. Modified medical syringe with a flow regulator for the administration of local anaesthetic, according to claim 1, wherein a distal end of the through-hole of the cylindrical body is located on a distal side of the cylindrical body is placed on an axis of revolution of the aforementioned body.

3. Modified medical syringe with a flow regulator for the administration of local anaesthetic, according to claim 1, wherein the proximal sides of the cap and a syringe barrel support define a single plane.

4. Modified medical syringe with a flow regulator for the administration of local anaesthetic, according to claim 3, wherein a proximal side of the syringe barrel support is equipped with a radial slot designed to house the flexible tube.

5. Modified medical syringe with a flow regulator for the administration of anaesthesia, according to claim 4, wherein the cylindrical cap and the support disk form a single piece.

6. Modified medical syringe with a flow regulator for the administration of local anaesthetic, according to claim 5, wherein the fluid pressurisation device is a syringe or an elastomer.

7. Modified medical syringe with a flow regulator for the administration of local anaesthetic, according to claim 6, wherein a connector between the syringe and the needle is of the "luer-lock" type.

8. Modified medical syringe with a flow regulator for the administration of local anaesthetic, according to claim 2, wherein the proximal sides of the cap and the support disk define a single plane.

9. Modified medical syringe with a flow regulator for the administration of local anaesthetic, according to claim 4, wherein the fluid pressurisation device is a syringe or an elastomer.

10. Modified medical syringe with a flow regulator for the administration of local anaesthetic, according to claim 3, wherein the fluid pressurisation device is a syringe or an elastomer.

11. Modified medical syringe with a flow regulator for the administration of local anaesthetic, according to claim 2, wherein the fluid pressurisation device is a syringe or an elastomer.

12. Modified medical syringe with a flow regulator for the administration of local anaesthetic, according to claim 1, wherein the fluid pressurisation device is a syringe or an elastomer.

13. Modified medical syringe with a flow regulator for the administration of local anaesthetic, according to claim 5, wherein a connector between the syringe and the needle is of the "luer-lock" type.

14. Modified medical syringe with a flow regulator for the administration of local anaesthetic, according to claim 4, wherein a connector between the syringe and the needle is of the "luer-lock" type.

15. Modified medical syringe with a flow regulator for the administration of local anaesthetic, according to claim 3, wherein a connector between the syringe and the needle is of the "luer-lock" type.

16. Modified medical syringe with a flow regulator for the administration of local anaesthetic, according to claim 2, wherein a connector between the syringe and the needle is of the "luer-lock" type.

17. Modified medical syringe with a flow regulator for the administration of local anaesthetic, according to claim 1, wherein a connector between the syringe and the needle is of the "luer-lock" type.

* * * * *